United States Patent [19]
Stenoien et al.

[11] Patent Number: 5,866,217
[45] Date of Patent: Feb. 2, 1999

[54] SILICONE COMPOSITE VASCULAR GRAFT

[75] Inventors: Mark D. Stenoien, Columbia Heights; William J. Drasler, Minnetonka; Robert J. Scott, Oak Grove; Mark L. Jenson, Greenfield, all of Minn.

[73] Assignee: Possis Medical, Inc., Minneapolis, Minn.

[21] Appl. No.: 787,227

[22] Filed: Nov. 4, 1991

[51] Int. Cl.⁶ ........................................ A61F 2/06
[52] U.S. Cl. .................. 428/36.3; 428/36.5; 428/36.91; 623/1
[58] Field of Search .................. 623/1, 9, 12; 428/36.3, 428/36.5, 36.91

[56] References Cited

U.S. PATENT DOCUMENTS

| | | | |
|---|---|---|---|
| 3,409,914 | 11/1968 | Jones | 3/1 |
| 3,713,441 | 1/1973 | Thomas | 128/214 |
| 3,823,705 | 7/1974 | Trimble | 128/1 |
| 3,866,247 | 2/1975 | Sparks | 3/1 |
| 3,866,609 | 2/1975 | Sparks | 128/303 |
| 3,890,107 | 6/1975 | White et al. | 29/183 |
| 3,929,971 | 12/1975 | Roy | 423/308 |
| 4,043,331 | 8/1977 | Martia et al. | 128/156 |
| 4,044,404 | 8/1977 | Martia et al. | 3/19 |
| 4,061,134 | 12/1977 | Samuels et al. | 128/1 |
| 4,127,706 | 11/1978 | Martin et al. | 429/122 |
| 4,323,525 | 4/1982 | Bornat | 264/24 |
| 4,345,414 | 8/1982 | Bornat et al. | 53/425 |
| 4,416,028 | 11/1983 | Eriksson et al. | 3/1.4 |
| 4,629,458 | 12/1986 | Pinchuk | 623/1 |
| 4,657,544 | 4/1987 | Pinchuk | 623/1 |
| 4,687,482 | 8/1987 | Hanson | 623/1 |
| 4,689,186 | 8/1987 | Bornat | 264/6 |
| 4,731,073 | 3/1988 | Robinson | 623/1 |
| 4,743,251 | 5/1988 | Barra | 623/1 |
| 4,834,746 | 5/1989 | Kira | 623/1 |
| 4,842,575 | 6/1989 | Hoffman, Jr. et al. | 600/36 |
| 4,878,908 | 11/1989 | Martin et al. | 623/1 |
| 4,906,465 | 3/1990 | Chaikof et al. | 424/78 |
| 4,969,896 | 11/1990 | Shors | 623/1 |
| 4,990,131 | 2/1991 | Dardik et al. | 600/36 |
| 5,037,377 | 8/1991 | Alonso | 600/36 |

*Primary Examiner*—Christopher Raimund
*Attorney, Agent, or Firm*—Hugh D. Jaeger

[57] ABSTRACT

A silicone composite vascular graft especially well suited as an arteriovenous (A-V) graft fistula for dialysis application. The graft has the ability to seal around needle puncture holes without externally applied pressure, excellent anti-kink, anti-crush and strength properties, and a smooth non-porous inner surface which reduces thrombus deposition and enhances the graft wall compliance or elasticity.

3 Claims, 2 Drawing Sheets

SILICONE COMPOSITE VASCULAR GRAFT

BACKGROUND OF THE INVENTION

1. Field of the Invention

The present invention pertains to a silicone/DACRON composite vascular graft, especially well suited as an arteriovenous (A-V) graft fistula for patients requiring long-term vascular access, such as in the case of chronic kidney dialysis.

2. Description of the Prior Art

Silicone grafts have been developed in the past using a variety of construction methods. The benefits of silicone material are described in U.S. Pat. 4,687,482. A DACRON outer support, which prevents aneurysm, is described in U.S. Pat. Nos. 4,657,544 and 4,629,458. White and Roy have patents which use silicone impregnated into sea urchin skeleton to form a porous structure one the skeleton is dissolved away; see U.S. Pat. Nos. 3,890,107 and 3,929,971.

An electrostatic spinning technology has been patented for use in primarily polyurethane grafts in U.S. Pat. Nos. 4,043,331; 4,044,404; 4,639,186; 4,127,706; 4,345,414; 4,323,525; and 4,878,908. These patents describe procedures used to spin polyurethane fibers. Without the addition of infra red (IR) curing as part of the immediate fiber curing process, the silicone fibers would meld together and form a clump.

SUMMARY OF THE INVENTION

The general purpose of the present invention is to provide a silicone/DACRON composite vascular graft for use as an artificial blood vessel, especially an arteriovenous (A-V) graft fistula providing long-term vascular access for kidney dialysis applications.

According to one embodiment of the present invention, there is provided a graft including a non-porous, smooth inner blood contact surface which reduces thrombus deposition; a silicone fiber porous structure; a silicone bead spiral or ring for anti-kink and anti-crush resistance; a DACRON (polyester fiber) yarn wind primarily for added strength; a small pore bulk construction with an impermeable inner surface which reduces fibroblast ingrowth and helps maintain compliance; continued elasticity, which allows excellent needle puncture sealing immediately and over time without applying external pressure; and silicone coating on the DACRON yard wind to prevent body tissue from contacting DACRON, which is a very thrombogenic material.

According to the process for constructing the one embodiment of the present invention, IR energy is used to partially cure the silicone fibers before they are deposited on the mandrel; the order of construction of the graft enhances the strength, anti-crush, and anti-kink characteristics; the angle of applying the DACRON yarn and its placement on top of the silicone bead allow the DACRON filaments to move relative to their repeat unit neighbor filaments to help reduce any tendency toward graft kinking; and the silicone is dispersed in solvent for electrostatic spinning.

In another embodiment of the present invention, the blood contacting surface of the graft can be of a fibrous porous construction similar, but not necessarily identical, in structure to the middle and outer porous structures of the first embodiment. The pore size may range from approximately 2 microns to 100 microns. The porous inner surface will allow cellular attachment to the inside surface of the graft. These cells may originate from cells located at the junction of the graft with the native vessel, from cells that grow through the walls of the graft from the outside tissue, or from the blood itself. The porous inner surface may enhance long-term patency of the graft in vascular grafting situations where the blood flow rate is relatively low.

In yet another embodiment of the present invention, the graft can be constructed without the DACRON yarn filament. The function of the graft will be suitable for most vascular graft applications, but the strength of the graft to resist aneurysm or suture pullout will be somewhat reduced.

The significant aspects, advantages and uniqueness of this graft and its process of fabrication in summary are the following: (1) the non-porous smooth silicone blood contact surface, which reduces thrombus deposit; (2) the bulk pore size and the solid inner surface, resulting in needle puncture sealing immediately and over time without applying external pressure; (3) the use of IR energy along with electrostatic spinning; (4) the application of a silicone bead for anti-kink and anti-crush resistance; (5) the application of DACRON yarn for strength without any significant reduction in anti-kink properties of the graft; (6) the coating of the DACRON yarn with silicone prior to its application onto the graft; and (7) the bulk pore size and solid inner surface which tends to allow reticulocyte penetration into the porous portion of the graft, but not much fibroblastic ingrowth, results in retaining graft compliance or elasticity over time.

Another significant aspect and feature of the process is construction which uses electrostatic spinning or spraying technology to form a fibrous and porous silicone structure that is found in much of the graft wall. This electrostatic technology is also used to apply the non-porous smooth silicone layer directly onto a mandrel, such layer forming the blood contact surface after removal of the graft from the mandrel.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
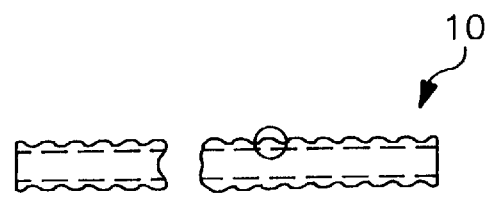
FIG. 1 illustrates a plan view of a vascular graft.

FIG. 1 illustrates a plan view of the vascular graft 10.

Figure 2:
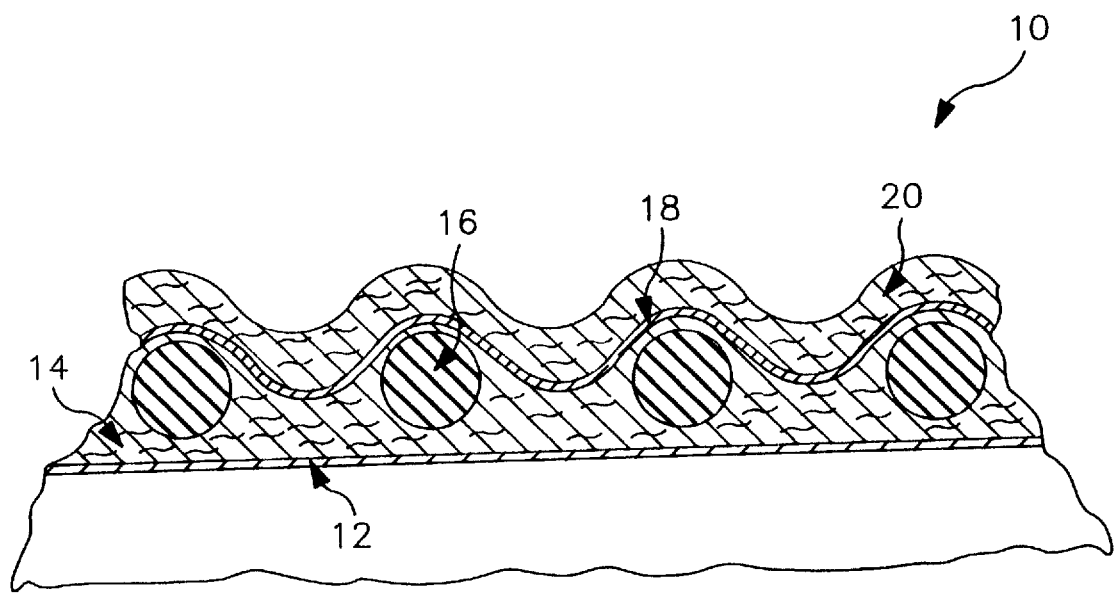
FIG. 2 illustrates an enlarged partial cross sectional view of the vascular graft in the area designated by the circle in FIG. 1.

FIG. 2 illustrates an enlarged partial cross sectional view of the vascular graft 10 in the area designated by the circle in FIG. 1. A meld layer 12 is first applied to a mandrel spinning at low rpm (approximately 200 rpm) with IR heater off, but with the electrostatic spinning voltages of the grid and mandrel activated. This allows a uniform layer of silicone to be deposited onto the mandrel forming a blood contact surface that is as smooth as the mandrel finish and that is impermeable to blood, plasma, or cellular penetration. The high flow rate of blood which will move through the graft 10 will help prevent thrombus deposition on the smooth surface. Since blood or plasma cannot penetrate this layer, this graft 10 does not require preclotting (a method required for some porous grafts whereby blood is allowed to clot within the graft wall to prevent seepage or bleeding through the graft walls). This non-porous inner meld layer 12 also reduces the amount of fibroblastic cell penetration into the graft 10 from the outside surface. Fibroblastic ingrowth generally results in the deposition of collagen within the pores of porous grafts and significantly reduces the flexibility of the graft over time. The reduction in fibroblastic ingrowth into the walls of this graft 10 allows it to remain flexible and thereby maintain its needle puncture hole sealing characteristic, as well as its flexibility and anti-kink properties.

The next layer, which is applied on top of the non-porous meld layer 12, is the porous silicone middle layer 14. To form individual fibers, the mandrel is spun at a much faster rate (approximately 4000 rpm). The IR heater and the electrostatic voltages are both activated. The silicone fibers are partially cured before they contact the mandrel due to the application of IR energy. The porosity or percent void fraction in a porous silicone structure of this layer can be controlled by adjusting the amount of fiber cure and the amount of melding of the fiber prior to deposition onto the mandrel. This layer 14 provides a fibrous structure of the graft 10 which serves as a framework to hold a silicone bead 16 and a DACRON yard 18 that are applied on top of it, and gives rise to a structure that can expand and compress and thereby contribute to the anti-kink character of the graft 10. This layer 14 also contributes to graft strength and needle puncture sealing. The pore spacing and silicone fiber diameter range from 2 to 100 microns with a generally random occurrence. The pore size is of appropriate size to allow reticulocyte penetration into the graft wall, but not so large as to allow entry access to significant fibroblast penetration. Reticulocytes are cells which can penetrate into the small pore spaces, but generally do not deposit significant collagenous material that can result in loss of graft elasticity and needle hole sealing characteristics.

A silicone bead 16 is then applied in a noncured form in a spiral configuration onto the porous middle layer 14 of the graft 10. This step is not done using electrostatics and involves simply extruding a silicone bead 16 onto a rotating graft 10 while moving transversely to form a spiral; the silicone bead 16 is then partially cured afterward. This spiral silicone bead 16 serves to enhance the graft 10 anti-kink and anti-crush properties by providing a structure which tends to maintain a circular cross section in the graft under compressive forces and forces which are generated when the graft 10 is bent to a radius of curvature of 1 cm or less. This spiral silicone bead 16 could be replaced with a series of torus shaped rings spaced approximately as far apart as each repeat unit of the spiral.

On top of the silicone bead, a polyethylene terephthalate (PET) or DACRON yard winding 18 is applied forming a series of spirals which are wound with both right-handedness and left-handedness winding directions. The presence of the DACRON yarn winding 18 provides strength to the graft 10 so that the graft 10 does not exhibit weakness axially or radially, with resultant aneurysm formation. The DACRON yard winding also contributes to enhance the pullout strength for sutures at the ends of the graft 10 where they are sewn to native vessels. The positioning of the DACRON yarn winding 18 over the silicone bead 16 allows the graft 10 to maintain excellent anti-kink characteristics. Each DACRON strand of the yarn winding can change its relative position to its neighboring repeat strand while the graft 10 is being bent, and thereby not inhibit bending. In addition, the presence of the DACRON strands in the graft wall tend to resist the formation of an oval cross section of the graft 10, and thereby contribute to enhanced anti-kink and anti-crush characteristics for the graft 10. The DACRON could be replaced by other biostable filamentous materials. Currently, the DACRON yarn is coated with silicone prior to its application onto the graft 10 to ensure that DACRON material is not put into direct contact with body tissue and to enhance DACRON to graft bonding.

An outer silicone layer 20 is applied using ELS spinning and IR energy. It provides a porous outer layer that allows tissue to ingrow and anchor it in place in the subcutaneous tissue of the patient. It also helps to hold the DACRON yarn winding 18 and silicone bead 16 in place. The pore structure of the outer porous layer 20 is similar to the pore structure of the middle porous layer 14 and retains its elasticity due to minimal fibroblastic ingrowth.

DESCRIPTION OF THE ALTERNATIVE EMBODIMENTS

Figure 3:
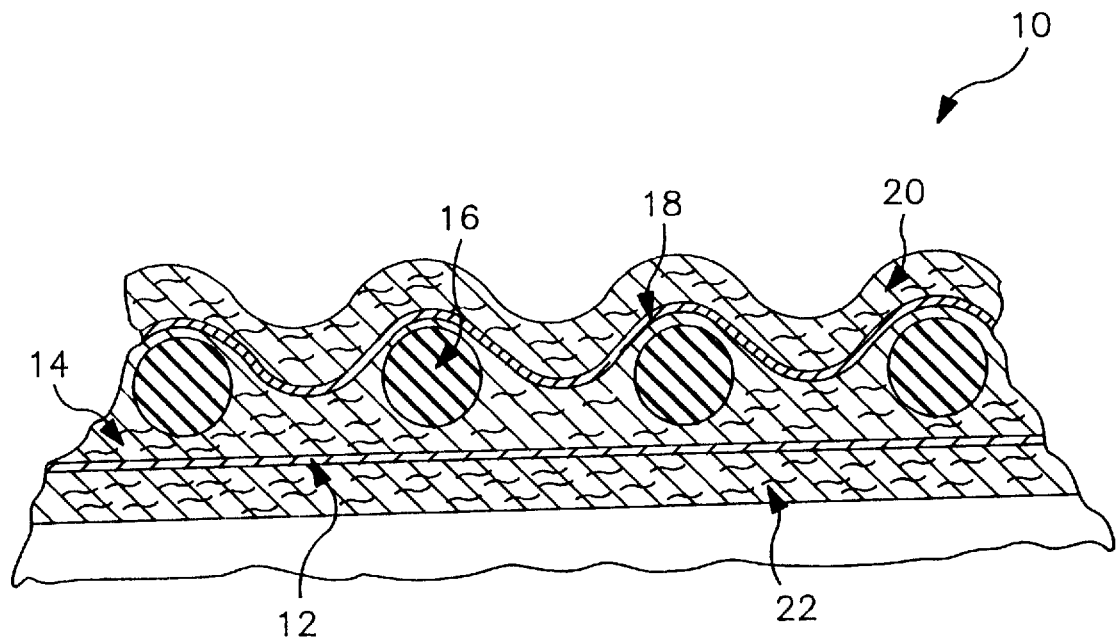
FIG. 3 is a view similar to FIG. 2 illustrating a first alternative embodiment; and, FIG. 4 is a view similar to FIG. 2 illustrating a second alternative embodiment.

The graft can be constructed in a manner identical with that of the preferred embodiment (FIG. 2), but with an additional porous silicone inner layer that is first applied onto the mandrel, as shown in FIG. 3. This additional inner layer 22 will allow tissue to attach to the graft inner surface. A meld layer 12 would then be applied second and would serve to prevent blood or plasma penetration through the graft wall.

Figure 4:
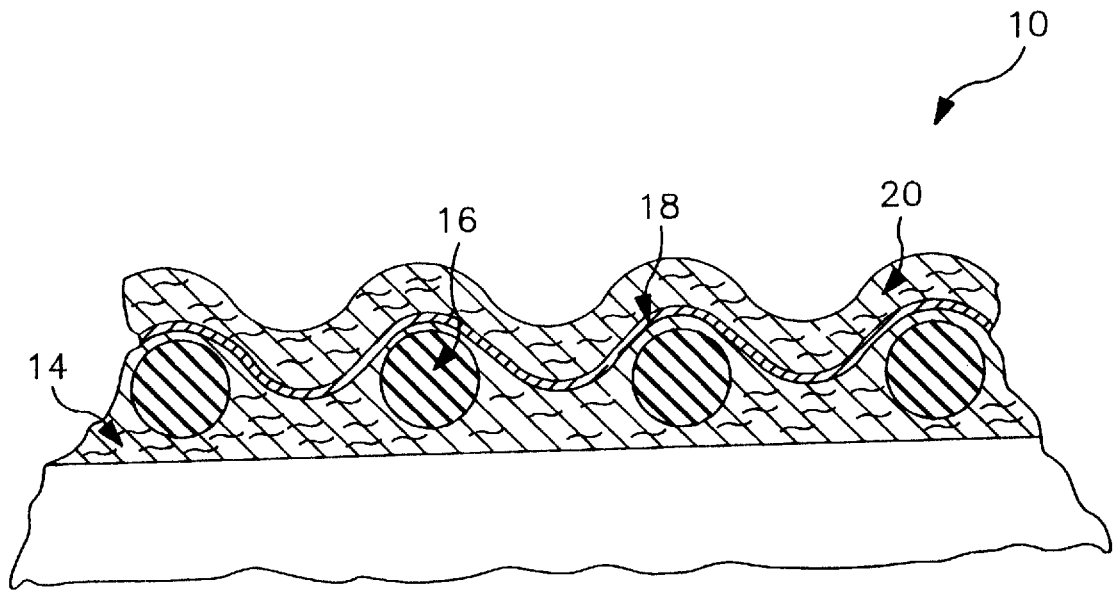

In yet another embodiment, shown in FIG. 4, the graft is constructed in a manner identical to that of the preferred embodiment (FIG. 2), but with the omission of the inner meld layer 12. With this construction, the inner surface consists of porous silicone fibers to allow good tissue attachment on the inner surface. In this case, the meld layer 12 is not present and tissue can penetrate through the entire wall of the graft from the outside of the graft to the inner surface.

In yet another embodiment, the graft can be constructed of another biostable polymeric material, other than silicone, that can be spun electrostatically.

In yet another embodiment, the PET filament material can be replaced by another biostable filament material to provide additional graft strength.

In yet another embodiment, the silicone material used for the bead can be replaced by another biostable polymeric material that can be bound to silicone, and provide the anti-kink characteristic of the graft.

Various modifications can be made to the present invention without departing from the apparent scope hereof. There can be a coating or layer of the porous silicone middle layer material between the silicone bead and the polyethylene terephthalate winding, although this is optional.

It is claimed:
1. Composite graft comprising in order:
   a. a porous silicone inner layer;
   b. a non-porous meld layer;
   c. a porous silicone middle layer;
   d. a silicone bead;
   e. a PET winding; and,
   f. a porous silicone outer layer.
2. A vascular graft comprised of:
   a. a fibrous porous wall providing a flexible structure which allows at least some tissue ingrowth and anchoring of the graft in the surrounding tissue;

b. said fibrous porous wall having at least a portion with pores sufficiently small to reduce fibroblast ingrowth into the graft wall;

c. said small-pore portion thereby allowing graft flexibility to be maintained over time; and, d. wherein said porous wall comprises a silicone material.

3. A vascular graft comprised of:

a. a fibrous porous wall providing a flexible structure for tissue ingrowth and anchoring of the graft in the surrounding tissue;

b. at least a portion of said fibrous porous wall being comprised of an elastomeric material such as silicone or polyurethane;

c. said elastomeric material providing resilience to resist crushing or kinking of the graft; and, d. a spiral bead or rings of polymeric material, said bead or rings providing enhanced kink resistance and crush resistance to the graft.

* * * * *